Sept. 1, 1942.
D. A. L. NAPIER
Plant Pat. 544
CARNATION PLANT
Filed March 12, 1942
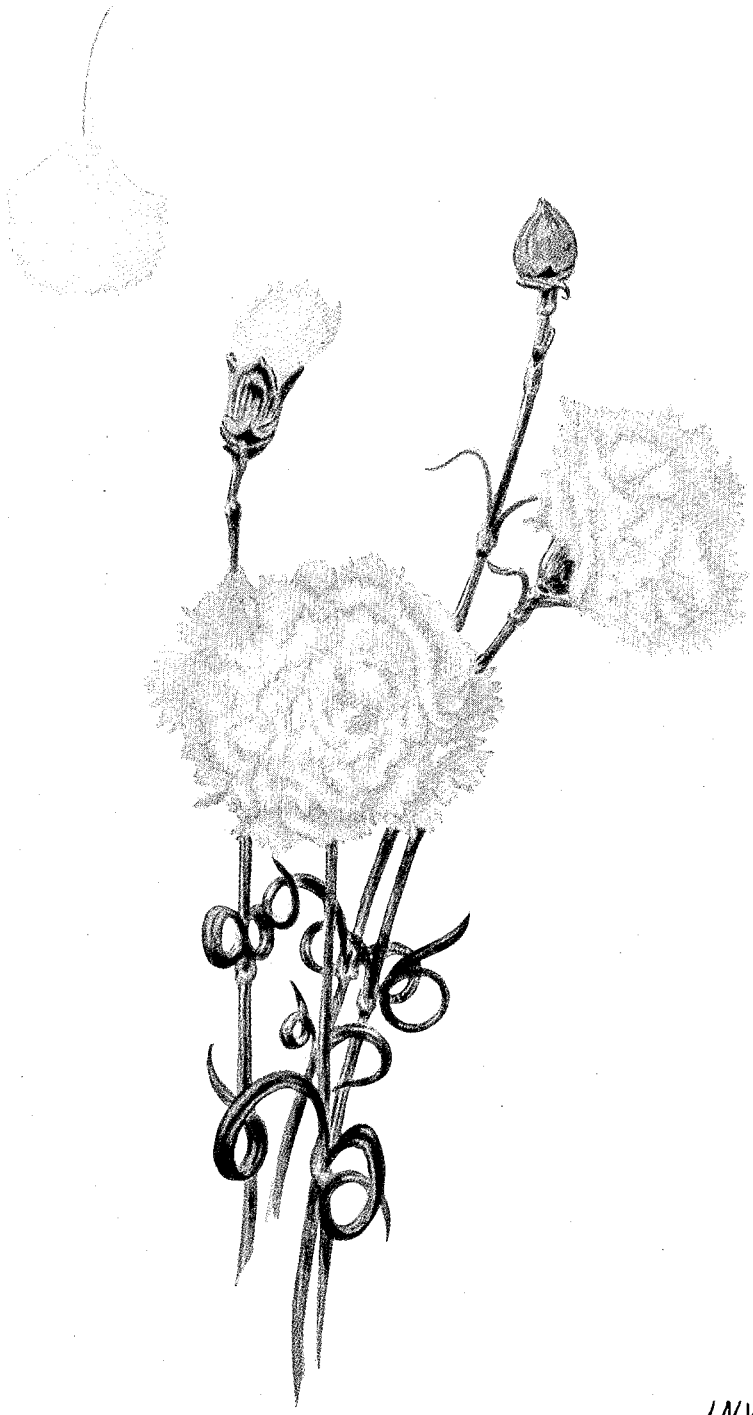
INVENTOR
Dorothy A. L. Napier
By Orville M. Kile
Plant Pat. Agt Patented Sept. 1, 1942

Plant Pat. 544

UNITED STATES PATENT OFFICE

544

CARNATION PLANT

Dorothy A. L. Napier, Taunton, England, assignor to Walter William Gammage, London, Ontario, Canada Application March 12, 1942, Serial No. 434,433

1 Claim. (Cl. 47—60)

My new invention relates to a carnation variety of the type commonly known as perpetual blooming or greenhouse forcing varieties.

The object of my invention is to produce a carnation variety of the deep pink class having large blossoms of a distinctive color and great brilliance, and at the same time having sturdy growth qualities.

My new carnation variety resulted from definite breeding efforts, having been derived from self-crossing the variety My Love. I have for a number of years experimented in the production of carnation varieties and this new variety is the finest deep pink I have seen. It has been reproduced asexually and its characteristics have become permanently fixed.

The original illustrations accompanying this application show a tight bud, an opening bud and two open flowers, together with stems and foliage of this new carnation variety. These are all portrayed in as nearly their true colors as the artist could depict them.

Following is a detailed description of the plant and flower. Color plate references indicate Ridgway's Color Standards and Nomenclature.

*The plant*

Growth: Vigorous; sturdy; tall; few side shoots and no tendency to "grassiness." Very easily rooted and propagated with practically no losses in the cutting bench. Can successfully be carried into the second and third year in greenhouse culture, a quality not frequently found among good carnation varieties now on the market.

Blooming habit: Exceedingly free-blooming.

Disease resistance: Very pronounced resistance to diseases common to carnations.

Stems: Medium length; stiff; medium in size but very strong; dark green color, approximately Dusky Yellowish Green (Plate XLI) with a light covering of bloom.

*Nodes:* Very close together on lower portion of stem, permitting the foliage to come close together.

Foliage: Long and curled at base of stem but uncurled and rather short at first two nodes next to blossom. Approximately same color as stems.

*The flower*

Bud: Tight bud is plump but sharply pointed at apex. Opening bud unfolds its petals and enlarges in size over a period of several days.

Blossom:

*Size.*—Large, averaging approximately 3½ inches in diameter.

*Shape.*—Regular with fairly high center.

*Petalage.*—Full-petaled, having from 60 to 70 petals in early April.

*Color.*—The color of the newly opened flower is very deep pink, brilliant but elusive. The popular designation of the color would be cerise. The color in Ridgway's which is most nearly like it is Rose Red (Plate XII). However it is slightly lighter than this color without having any of the purple or blue tones found in Rose Color which is the next in the scale. Rather, its brilliance is heightened by slight suggestions of the tones of Spectrum Red (Plate I), these latter tones appearing more in evidence when viewed in artificial light. As the flower ages it loses much of its brilliance and in its final stage before withering it approaches Rose Color (Plate XII).

*Fragrance.*—Pleasing; mild.

*Calyx.*—Exceedingly tough and strong, never known to split. Color ranges from Lettuce Green (Plate V) at the base to Cerro Green (Plate V) at the top. *Bracts* are short, sharp and tough.

Reproductive organs:

*Pistils.*—Two; very long; usually visible in the open flower; curled at upper end; white; heavy; protruding from high ovary.

*Stamens.*—Few; white; uneven lengths.

*Ovary.*—Large; high; many ovules; case tough.

Having thus disclosed my invention, I claim:

The carnation variety herein shown and described, characterized particularly by its ease of propagation; its great degree of success in being carried over into the second and third years in greenhouse culture; its very prolific production of blossoms; the sturdy nature of the calyx; and the distinctive brilliant cerise color of its large blossoms as indicated.

DOROTHY A. L. NAPIER.